(12) United States Patent
McDermott et al.

(10) Patent No.: US 10,398,578 B2
(45) Date of Patent: *Sep. 3, 2019

(54) STENT WITH A BIO-RESORBABLE CONNECTOR

(71) Applicant: C.R. Bard, Inc., Murray Hill, NJ (US)

(72) Inventors: John D. McDermott, Coto De Caza, CA (US); Khoi Q. Ta, San Jose, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 69 days.

This patent is subject to a terminal disclaimer.

(21) Appl. No.: 15/652,083

(22) Filed: Jul. 17, 2017

(65) Prior Publication Data

US 2017/0312104 A1   Nov. 2, 2017

Related U.S. Application Data

(60) Division of application No. 14/169,087, filed on Jan. 30, 2014, now Pat. No. 9,707,110, which is a
(Continued)

(51) Int. Cl.
| | |
|---|---|
| *A61F 2/82* | (2013.01) |
| *A61F 2/91* | (2013.01) |
| *A61F 2/88* | (2006.01) |
| *A61F 2/915* | (2013.01) |
| *A61L 31/14* | (2006.01) |

(52) U.S. Cl.
CPC ............. *A61F 2/88* (2013.01); *A61F 2/91* (2013.01); *A61F 2/915* (2013.01); *A61L 31/148* (2013.01); *A61F 2002/91508* (2013.01); *A61F 2002/91533* (2013.01); *A61F 2002/91558* (2013.01); *A61F 2002/91575* (2013.01); *A61F 2220/0016* (2013.01); *A61F 2220/0058* (2013.01); *A61F 2250/0031* (2013.01)

(58) Field of Classification Search
CPC ................. A61F 2/82; A61F 2/91; A61F 2/88
USPC ............................................... 623/1.15–1.38
See application file for complete search history.

(56) References Cited

U.S. PATENT DOCUMENTS

| | | |
|---|---|---|
| 5,242,759 A | 9/1993 | Hall |
| 5,755,770 A | 5/1998 | Ravenscroft |

(Continued)

FOREIGN PATENT DOCUMENTS

| | | |
|---|---|---|
| CA | 2626717 A1 | 7/2007 |
| WO | 2004/045474 A1 | 6/2004 |

(Continued)

OTHER PUBLICATIONS

EP 06846747 filed Jun. 17, 2008 Extended European Search Report dated May 15, 2009.
(Continued)

*Primary Examiner* — Suzette J Gherbi
(74) *Attorney, Agent, or Firm* — Rutan & Tucker, LLP

(57) ABSTRACT

A stent including a plurality of curved sections and a connector. The curved sections surround a longitudinal axis to define a tube portion and are distributed along the longitudinal axis to form a helix. The connector includes a bioresorbable material and is positioned between two adjacent curved sections. The stent has a spring constant that changes to a different spring constant after exposure to biological material.

20 Claims, 11 Drawing Sheets

Related U.S. Application Data continuation of application No. 12/983,653, filed on Jan. 3, 2011, now Pat. No. 8,647,379, which is a continuation of application No. 12/096,902, filed as application No. PCT/US2006/062479 on Dec. 21, 2006, now Pat. No. 7,862,607.

(60) Provisional application No. 60/755,330, filed on Dec. 30, 2005.

(56) References Cited

U.S. PATENT DOCUMENTS

| | | | |
|---|---|---|---|
| 5,824,046 A | 10/1998 | Smith et al. | |
| 6,258,117 B1* | 7/2001 | Camrud | A61F 2/82 623/1.16 |
| 6,287,332 B1* | 9/2001 | Bolz | A61F 2/82 623/1.12 |
| 6,485,510 B1 | 11/2002 | Camrud et al. | |
| 6,730,117 B1 | 5/2004 | Tseng et al. | |
| 6,866,669 B2 | 3/2005 | Buzzard et al. | |
| 6,939,352 B2 | 9/2005 | Buzzard et al. | |
| 7,214,759 B2* | 5/2007 | Pacetti | A61L 31/10 424/422 |
| 7,445,792 B2* | 11/2008 | Toner | A61M 31/002 424/423 |
| 7,862,607 B2* | 1/2011 | McDermott | A61F 2/88 623/1.16 |
| 8,109,991 B2 | 2/2012 | Clifford et al. | |
| 8,500,793 B2 | 8/2013 | Zipse et al. | |
| 8,647,379 B2* | 2/2014 | McDermott | A61F 2/88 623/1.16 |
| 9,707,110 B2* | 7/2017 | McDermott | A61F 2/88 |
| 2002/0107560 A1 | 8/2002 | Richter | |
| 2002/0183826 A1 | 12/2002 | Dorn et al. | |
| 2003/0135265 A1* | 7/2003 | Stinson | A61F 2/90 623/1.16 |
| 2004/0167616 A1 | 8/2004 | Camrud et al. | |
| 2004/0220660 A1* | 11/2004 | Shanley | A61F 2/91 623/1.16 |
| 2005/0010279 A1 | 1/2005 | Tenerz et al. | |
| 2005/0090890 A1 | 4/2005 | Wu et al. | |
| 2005/0110214 A1 | 5/2005 | Shank et al. | |
| 2005/0222671 A1 | 10/2005 | Schaeffer et al. | |
| 2005/0287287 A1 | 12/2005 | Parker et al. | |
| 2006/0079955 A1* | 4/2006 | Brown | A61F 2/88 623/1.22 |
| 2006/0129233 A1 | 6/2006 | Eder et al. | |
| 2006/0217795 A1* | 9/2006 | Besselink | A61B 17/11 623/1.15 |
| 2007/0208421 A1 | 9/2007 | Quigley | |
| 2007/0282425 A1* | 12/2007 | Kleine | A61F 2/88 623/1.15 |
| 2008/0262599 A1 | 10/2008 | Caro et al. | |
| 2009/0204200 A1* | 8/2009 | Bales, Jr. | A61F 2/88 623/1.16 |
| 2009/0259294 A1* | 10/2009 | Cully | A61F 2/07 623/1.22 |
| 2010/0004725 A1* | 1/2010 | Zipse | A61F 2/91 623/1.2 |
| 2010/0023108 A1* | 1/2010 | Toner | A61F 2/91 623/1.11 |
| 2010/0049304 A1* | 2/2010 | Clifford | A61F 2/91 623/1.16 |
| 2010/0055295 A1* | 3/2010 | Hossainy | B05B 12/20 427/2.25 |
| 2010/0070024 A1* | 3/2010 | Venturelli | A61F 2/90 623/1.22 |
| 2010/0131044 A1* | 5/2010 | Patel | A61F 2/915 623/1.16 |
| 2010/0168841 A1* | 7/2010 | Furst | A61L 27/047 623/1.42 |
| 2010/0249904 A1* | 9/2010 | Takayuki | A61F 2/91 623/1.16 |
| 2010/0274347 A1* | 10/2010 | Boyle | A61F 2/91 623/1.15 |
| 2010/0331961 A1* | 12/2010 | Goetzen | A61F 2/915 623/1.16 |
| 2011/0184507 A1* | 7/2011 | Fischer, Jr. | A61F 2/91 623/1.16 |
| 2014/0148896 A1 | 5/2014 | McDermott et al. | |
| 2015/0306282 A1* | 10/2015 | Scanlon | A61L 31/14 623/1.11 |
| 2016/0045345 A1* | 2/2016 | Huang | A61F 2/91 623/1.16 |
| 2016/0184114 A1* | 6/2016 | Cottone, Jr. | A61F 2/82 623/1.15 |

FOREIGN PATENT DOCUMENTS

| | | |
|---|---|---|
| WO | 2005122960 A2 | 12/2005 |
| WO | 2006029617 A1 | 3/2006 |

OTHER PUBLICATIONS

PCT/US2006/062479 filed Dec. 21, 2006 International Preliminary Report on Patentability dated Jul. 1, 2008.

PCT/US2006/062479 filed Dec. 21, 2006 International Search Report dated Dec. 17, 2007.

PCT/US2006/062479 filed Dec. 21, 2006 Written Opinion dated Dec. 17, 2007.

U.S. Appl. No. 12/096,902, filed Dec. 30, 2008 Non-Final Office Action dated May 17, 2010.

U.S. Appl. No. 12/983,653, filed Jan. 3, 2011 Advisory Action dated Jan. 16, 2013.

U.S. Appl. No. 12/983,653, filed Jan. 3, 2011 Final Office Action dated Jul. 26, 2013.

U.S. Appl. No. 12/983,653, filed Jan. 3, 2011 Final Office Action dated Nov. 19, 2012.

U.S. Appl. No. 12/983,653, filed Jan. 3, 2011 Non-Final Office Action dated Feb. 26, 2013.

U.S. Appl. No. 12/983,653, filed Jan. 3, 2011 Non-Final Office Action dated May 24, 2012.

* cited by examiner

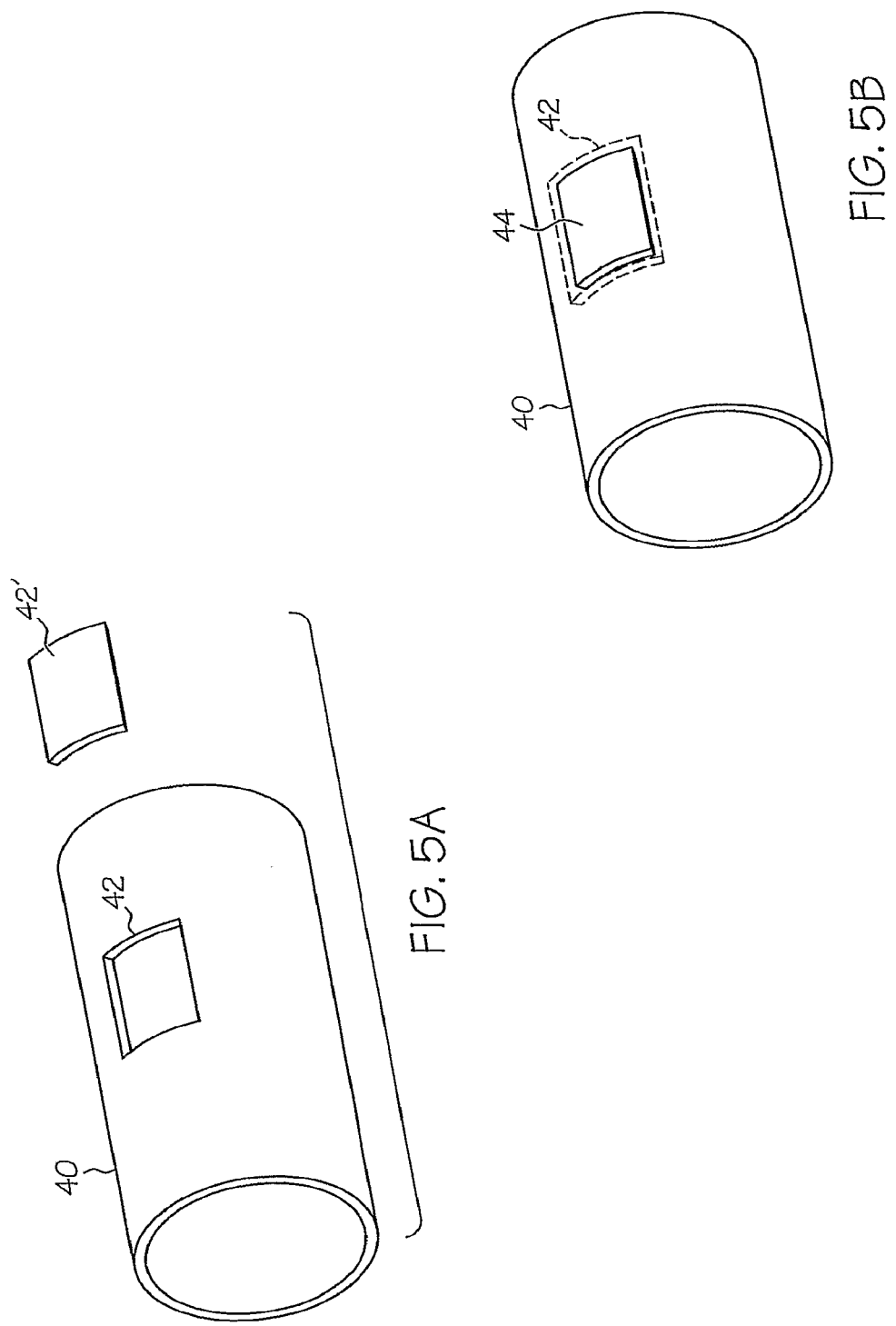

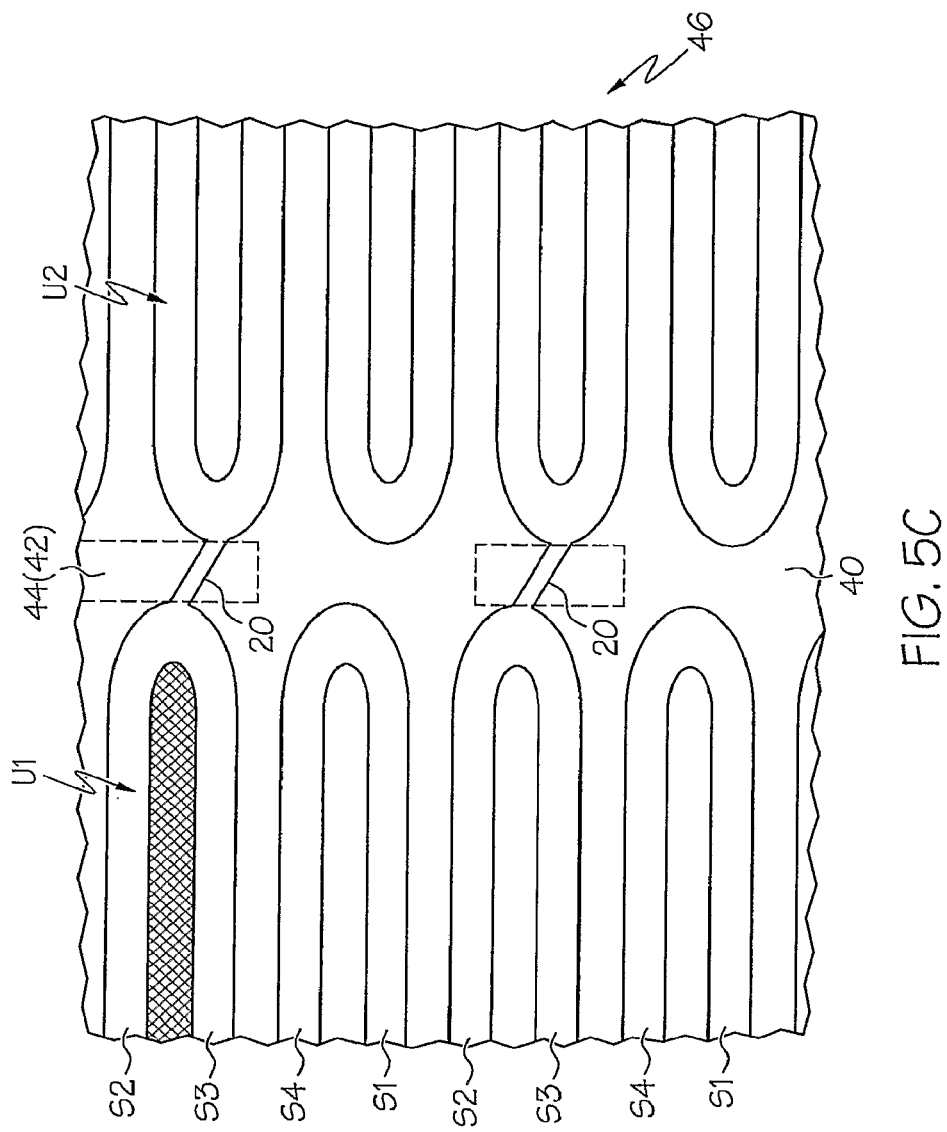

STENT WITH A BIO-RESORBABLE CONNECTOR

PRIORITY

This application is a continuation of U.S. patent application Ser. No. 14/169,087, filed Jan. 30, 2014, now U.S. Pat. No. 9,707,110, which is a continuation of U.S. patent application Ser. No. 12/983,653, filed Jan. 3, 2011, now U.S. Pat. No. 8,647,379, which is a continuation of U.S. patent application Ser. No. 12/096,902, now U.S. Pat. No. 7,862,607, which is a U.S. national stage application under 35 USC § 371 of International Application No. PCT/US2006/062479, filed Dec. 21, 2006, which claims benefit of priority to U.S. Provisional Patent Application No. 60/755,330, filed Dec. 30, 2005, each of which is incorporated by reference in its entirety into this application.

BACKGROUND

It is known in the medical field to utilize an implantable prosthesis to support a duct or vessel in a mammalian body. One such prosthesis may include a frame-like structure. Such frame-like structures are commonly known as a "stent", "stent-graft" or "covered stent." For the purpose of discussion, these structures are referred to collectively herein as a "stent."

The stent can be utilized to support a duct or vessel in the mammalian body that suffers from an abnormal widening (e.g., an aneurysm, vessel contraction or lesion such as a stenosis or occlusion), or an abnormal narrowing (e.g., a stricture). Stents are also utilized widely in the urethra, esophagus, biliary tract, intestines, arteries, veins, as well as peripheral vessels. The stent can be delivered via a small incision on a host body. Hence, the use of stents as a minimally invasive surgical procedure has become widely accepted.

The stents can be cut from a tube or wound from a wire on a mandrel. Thereafter, the stents can be expanded in the duct or vessel of a host by a separate mechanism (e.g., balloon) or by utilization of a material that self-expands upon predetermined implantation conditions.

One common form of the stent is configured as a series of essentially identical rings connected together to form a lattice-like framework that defines a cylindrical or tubular framework. The series of rings may or may not have connecting linkages between the adjacent rings. One example does not utilize any connecting linkages between adjacent rings as it relies upon a direct connection from one ring to the next ring. It is believed that more popular examples utilize connecting linkages between adjacent rings, which can be seen in stent products offered by various companies in the marketplace.

All of the above stent examples utilize a biocompatible metal alloy (e.g., Nitinol or Elgiloy). The most common metal alloy utilized by these examples is Nitinol which has strong shape memory characteristics so that Nitinol self-expand when placed in the duct or vessel of a mammalian body at normal body temperature. In addition to self-expansion, these stents utilize a series of circular rings placed adjacent to each other to maintain an appropriate longitudinal spacing between each rings. These stents are also intended to be a permanent implant in that removal subsequent to implantation requires major invasive surgery.

Recently, however, stents are being investigated for use in a host as a temporary implant by having the stents degrade or absorbed by the host body. The primary advantage of such temporary stents is the elimination of additional surgery to remove the stent after it has served its function of dilating a lesion or stenosis in the vessel or duct. The entire stent is believed to be resorbed by the host body after a period of time after implantation.

More recently, a combination of the features of the permanent stent and the bio-resorbable stent are also known. For example, U.S. Patent Publication No. US 2005/0222671 (published Oct. 6, 2005) shows and describes a series of connected annular rings with some of the connectors being biodegradable over time. U.S. Pat. No. 6,258,117 shows and describes at least a series of rings made from a biocompatible material (e.g., metal alloys) connected to each other via breakable or biodegradable links or connectors.

It is believed that these examples of partially biodegradable stents present a potential problem in that once the connecting linkages have biodegraded, the separated or unjoined annular rings could be susceptible to migration in the host body. It is believed that in a situation where the connector linkages have degraded faster than tissue incorporation (e.g., endothialization) of the annular rings, the rings could have the ability to migrate away from the original implantation site. Where the stent is a covered stent (i.e., a stent-graft), it is also believed that migration of discrete sections of the stent-graft could occur.

There is thus a need for an implantable prosthesis device that maintains the patency of a vessel with little or no ability to migrate from the implantation site while maintaining the patency of the duct or vessel of the host.

BRIEF SUMMARY OF THE INVENTION

Accordingly, the present invention relates to an implantable medical device that has various spring rates or spring constant to permit a change in the flexibility of the stent subsequent to implantation while maintaining various components of the device unitary which tends to alleviate a potential problem for stent migration for the known stents.

One embodiment includes a stent that includes a plurality of arcuate sections and at least one connector. The plurality of arcuate sections circumscribes a longitudinal axis from a first portion to a second portion to define essentially a portion of a tube. The arcuate sections are spaced apart along the longitudinal axis to form at least one continuous helical path about the longitudinal axis. The at least one connector is arranged to connect one arcuate section to an adjacent axially spaced arcuate section. The at least one connector is made from a material that is bioresorbed upon exposure to biological tissue such that the stent has a first spring constant in an unimplanted condition and a second different spring constant in an implanted condition after a predetermined period of time.

A further embodiment includes a method of deploying a stent. The method can be achieved by providing a stent having at least a portion of the stent bio-resorbable or biodegradable, the stent having a first spring constant; and changing the first spring constant of the stent to a second helical spring constant different than the first upon exposure to biological materials.

Another embodiment includes a stent. The stent can be in the configuration of a helical that includes a plurality of arcuate sections and at least one connector between adjacent arcuate sections. The plurality of arcuate sections circumscribes a longitudinal axis from a first portion to a second portion to define essentially a portion of a tube. The arcuate sections are spaced apart along the longitudinal axis to form at least one continuous helical path about the longitudinal axis. The at least one connector connects one arcuate section to an adjacent arcuate section and configured to be absorbed upon exposure to biological tissue.

Yet another embodiment includes a method of making a stent. The method can be achieved by forming a plurality of openings through a circumferential surface of a generally tubular member; filling each of the openings with a bioresorbable member to provide for a continuous circumferential surface of the tubular member; and removing materials from the circumference of the generally tubular member to define a plurality of struts.

These and other embodiments, features and advantages will become apparent to those skilled in the art when taken with reference to the following more detailed description of the invention in conjunction with the accompanying drawings that are first briefly described.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIGS. 5A-5D illustrate graphically the process of making the stent of FIG. 1.

DETAILED DESCRIPTION OF THE PREFERRED EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

FIGS. 1-6 are graphical representations of the preferred embodiments.

Figure 1:
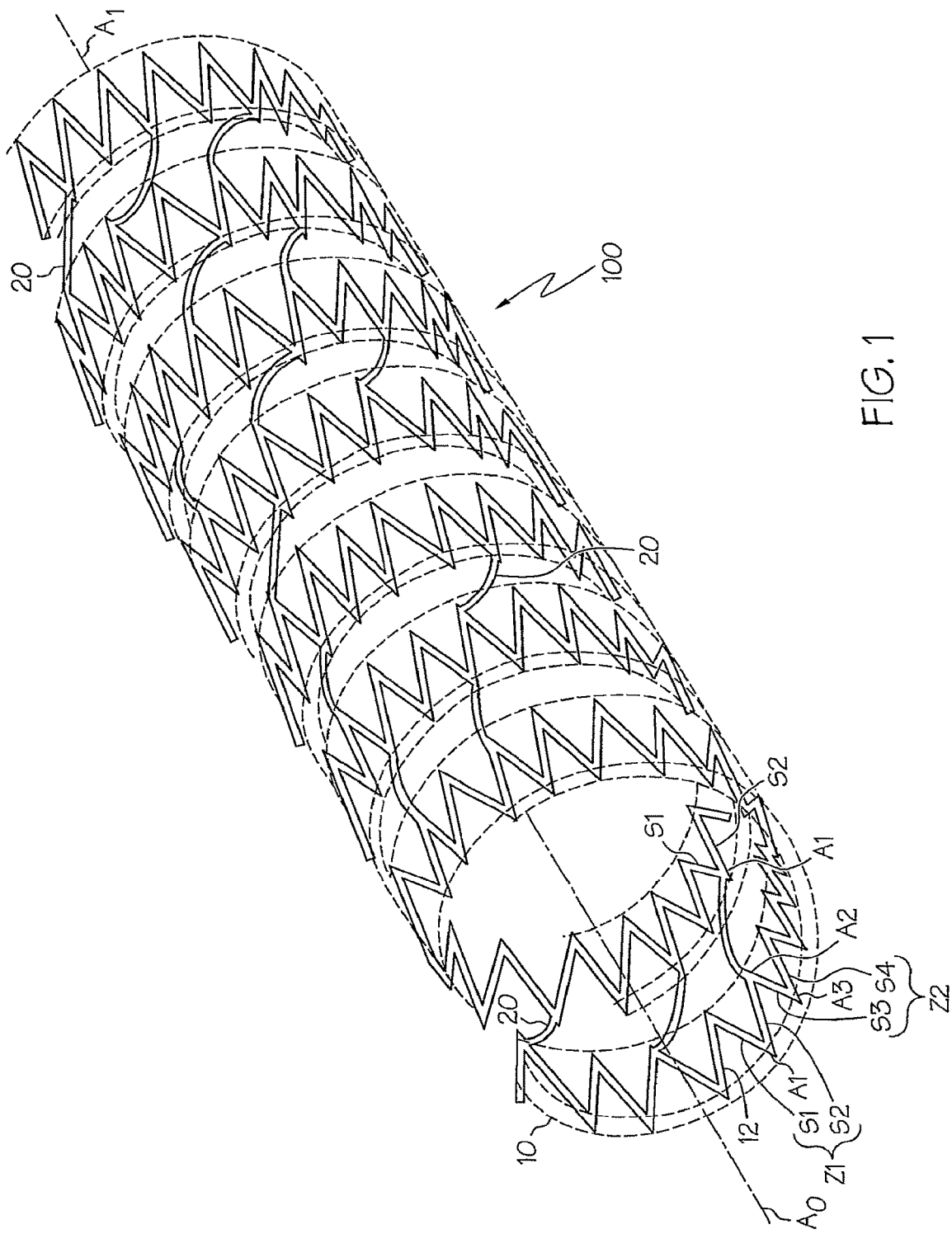
FIG. 1 illustrates an embodiment of the helical stent in a perspective view.

FIG. 1 illustrates a preferred embodiment of the helical stent 100 in a perspective view. The stent defines a generally cylindrical structure about a longitudinal axis $A_0$-$A_1$. To aid the viewer in visualization of the helical path 10 about the axis $A_0$-$A_1$ as defined by the zig-zag struts 12 of the stent 100, the helical path 10 is illustrated as two dashed lines generally circumscribing about the axis $A_0$-$A_1$, having a first end $A_0$ and a second end $A_1$. To further aid visualization, the stent 100 illustrated in FIGS. 1 and 2 displays only the foreground structure of the stent 100, with the background structure (such as the struts 12 continuing along the helical path 10 in the background) not displayed or only symbolically illustrated. It is noted that where the application of a covered stent is desired, the path 10 is also a representation of another embodiment where the struts 12 are covered (partially or wholly) by a suitable material (e.g., ePTFE, Dacron, Nylon, fibrin, to name a few).

The zig-zag struts 12 can be simplified to a repeating pattern of two struts, a strut S1 and a strut S2. A first strut pair Z1 of the struts S1 and S2 define a first apex A1 extending towards the first end $A_0$. When the first strut pair Z1 is coupled to a second strut pair Z2 of struts, having struts S3 and S4 and defining a second apex A3, the point where the first strut pair Z1 is connected to the second strut pair Z2 defines a connecting apex A2 extending away from the first end $A_0$. A plurality of strut pairs of Z1 and Z2 can be coupled and located on the helical path 10 as the path generally circumscribes the axis $A_0$-Ai. Although the strut pair Z1 is shown as generally identical to the strut pair Z2, each of the strut pairs can be of a different configuration. For example, the struts S1-S4 may be identical in the central portion of the stent and different proximate the ends of the stent and vice versa (e.g., different in the central portion and identical proximate the ends of the stent).

Figure 2:
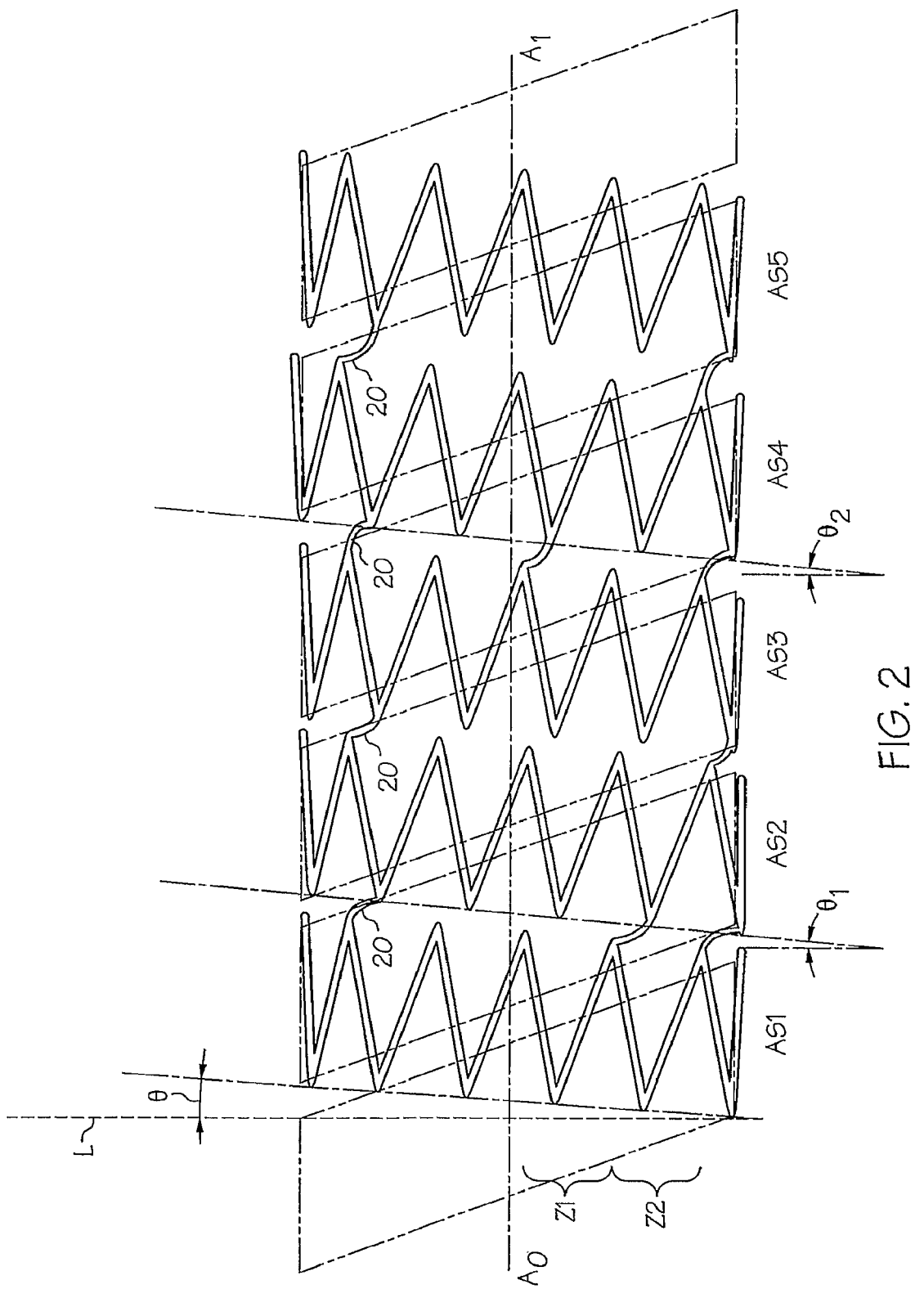
FIG. 2 is a side view of the structure of the stent of FIG. 1.

In circumscribing and translating along the axis, the helical path 10 follows a portion of a complete circle while at the same time translating along the axis $A_0$-$A_1$. As such, a plurality of arcuate sections AS (labeled as $AS_1$, $AS_2$, $AS_3$, $AS_4$, and $AS_5$ in FIG. 2) defined by the successive pairing of strut pairs Z1 and Z2 circumscribes the axis $A_0$-Ai from a terminal first end to a terminal second end of the helical path 10, to thereby define essentially a portion of a tube as illustrated in FIG. 1. The arcuate sections AS are spaced apart along the axis $A_0$-Ai to form at least one continuous helical path 10 about the axis $A_0$-$A_1$. As illustrated in FIG. 2, each of the arcuate sections AS form an angle with respect to the axis $A_0$-$A_1$ to define a respective helical angle θ with respect to a plane L intersecting and orthogonal to the axis $A_0$-$A_1$. The helical angle θ can be different for each arcuate section AS. Two or more helical segments, made of one or more arcuate sections AS, can be provided with different geometries by coupling one arcuate section AS2 having one helical angle $θ_1$ and another arcuate section AS4 having another helical angle $θ_2$ different from the one helical angle $θ_1$, as illustrated in FIG. 2.

The strut pairs Z1 and Z2 of each arcuate section AS are expandable and provide radial expandability to the arcuate section AS such that the plurality of arcuate sections AS have an unexpanded insertion size (FIGS. 5C-5D) and a larger expanded size (FIGS. 1-4 and 6) upon implantation. The expanded arcuate sections AS include a plurality of struts S1-S4 that extend in different directions with respect to the direction of the axis $A_0$-$A_1$.

Each of the arcuate sections AS may be connected to adjacent arcuate sections AS via a link or connector 20. In the preferred embodiments, the connector 20 couples the apex of a strut pair on one arcuate section to the apex of another strut pair on another arcuate section. At least one connector 20 is configured to be absorbed upon exposure to biological tissue.

Figure 3A:
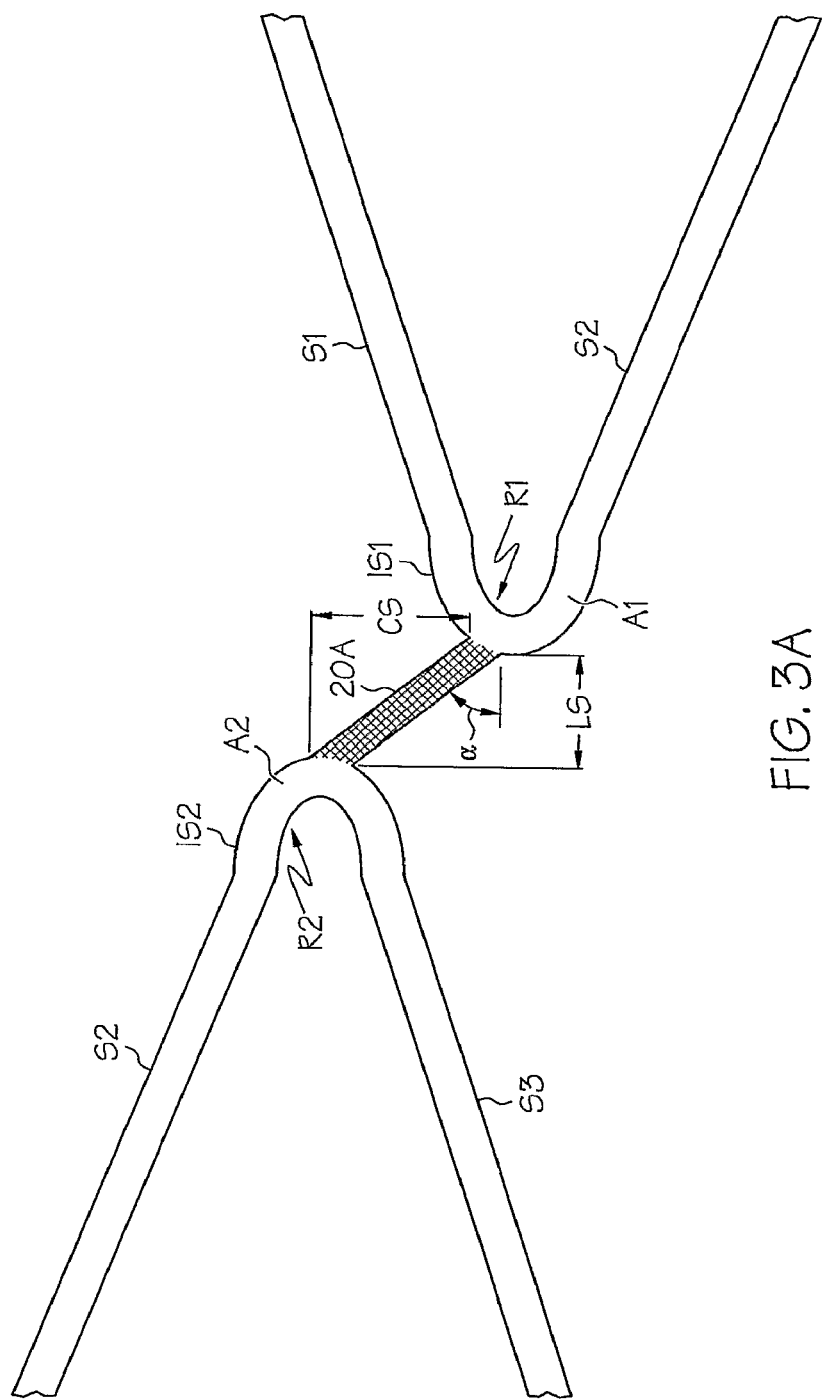
FIG. 3A is a close-up side view of a connector disposed between two helical struts of FIG. 1.
Figure 3B:
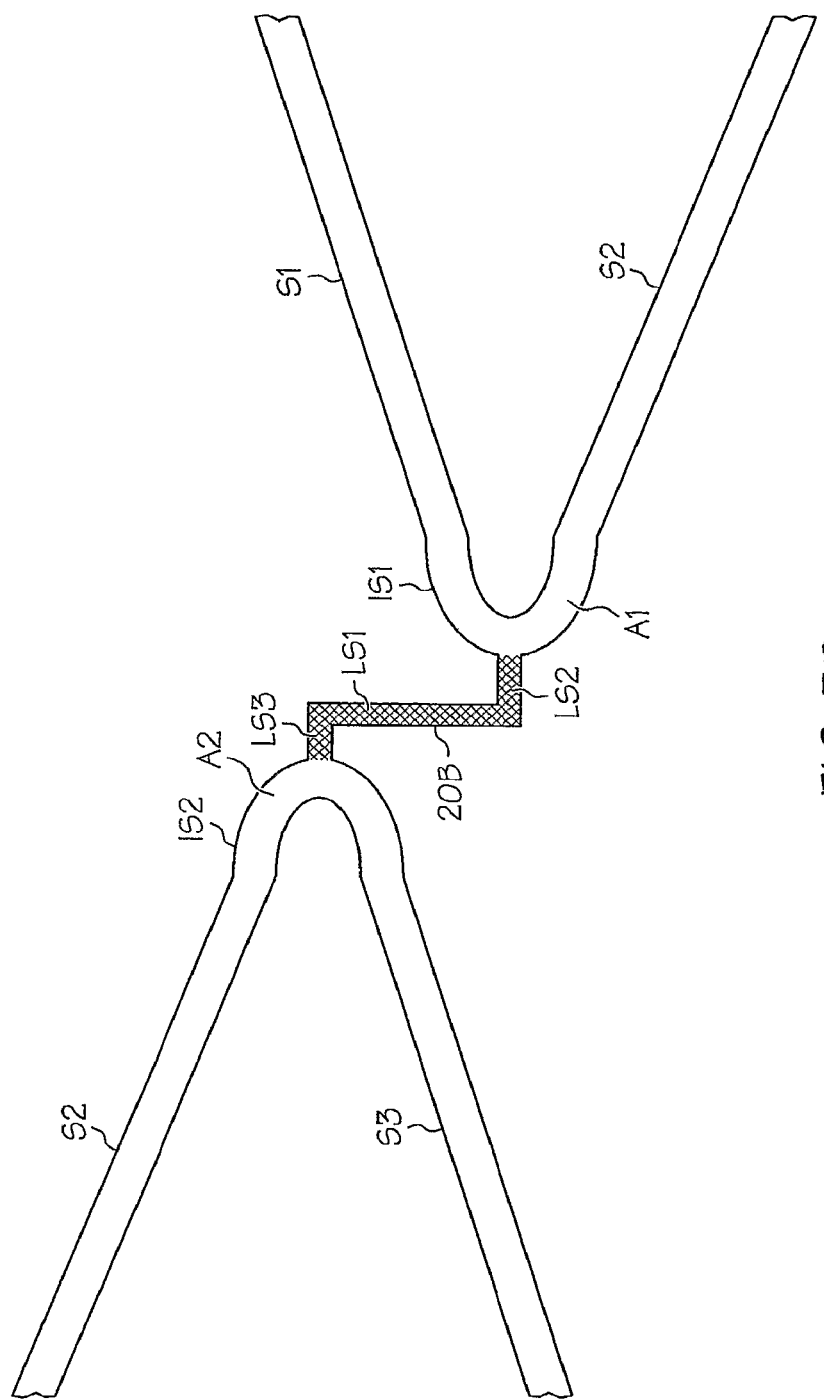
FIG. 3B is a variation of the connector illustrated in FIG. 3A.
Figure 3C:
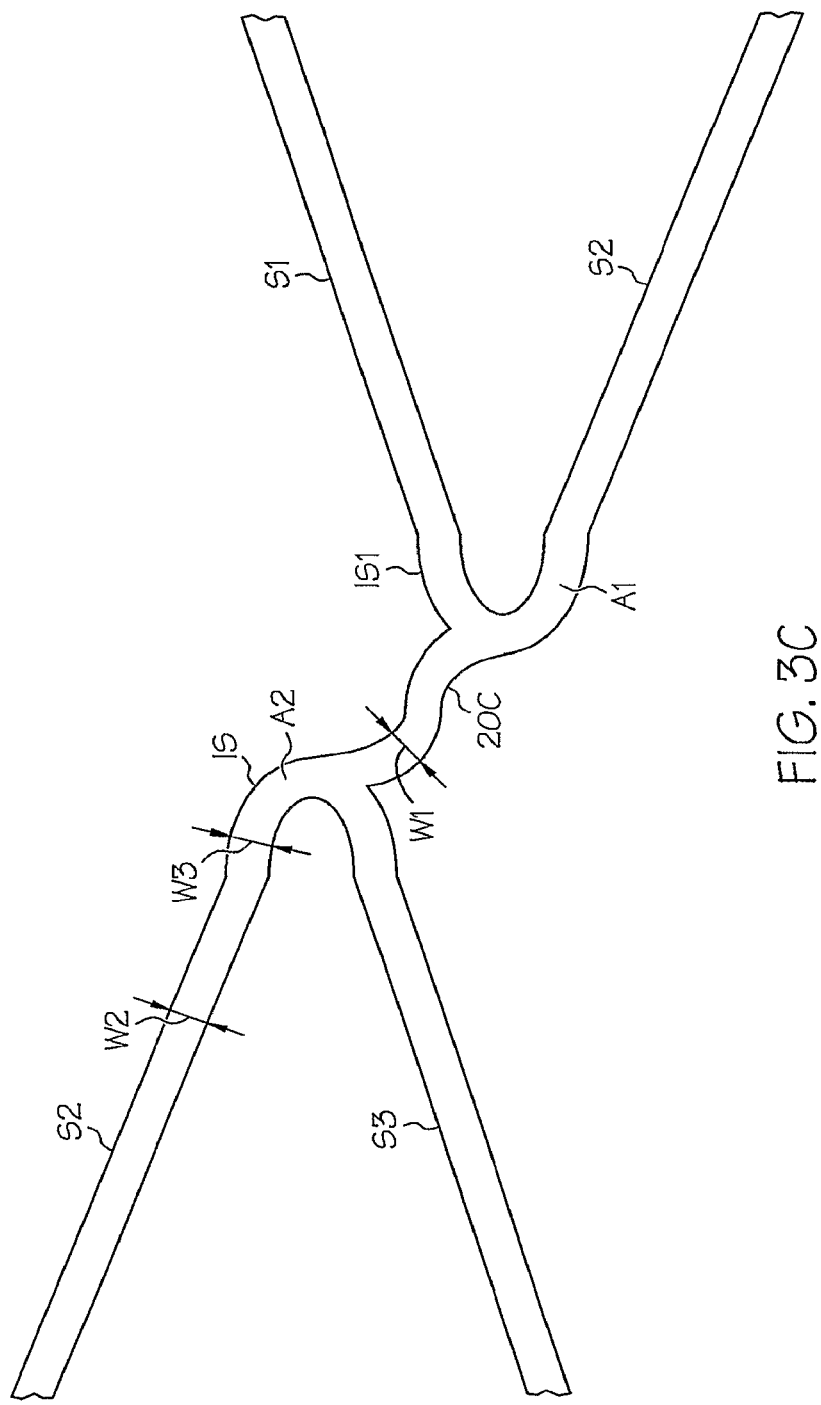
FIG. 3C is another variation of the connector illustrated in FIG. 3A.

Details of such connection between arcuate sections AS are illustrated and described in FIGS. 3A-3C. In FIG. 3A, the connector 20A is a generally linear connector that extends from the connecting apex A2 (or as close as technically feasible from the apex or outermost surface of the intersection of struts S2 and S3) to the first apex A1. The connector 20A is oriented at an angle α with respect to the axis $A_0$-$A_1$. When the stent illustrated in FIG. 3A is superimposed on a planar viewing surface, the apices A1 and A2 are offset at a circumferential distance CS and a longitudinal distance LS. The struts S1-S4 of the strut pairs Z1 and Z2 can be connected directly to each other as illustrated in FIG. 2 or coupled together via a curved intermediate member IS, illustrated as intermediate member IS1 and intermediate member IS2 in FIG. 3A. The curved intermediate member IS can include any suitable curve as long as the curved intermediate member IS functions to reduce stress concentration that can be generated when two generally linear members (struts S1-S4 as illustrated in FIG. 2) are connected directly to each other. In the preferred embodiments, the curved member IS have a radius with a curvature R, with a curvature R1 for the first apex A1 and a curvature R2 for the connecting apex A2 as illustrated in FIG. 3A. Curvatures R1 and R2, and curvature R3 (not shown), for second apex A3, can generally be equal different from each other.

In FIG. 3B, the connector 20B is formed of three generally linear segments LS1, LS2, and LS3 such that the connector extends in three directions that are each not oblique to the direction of the axis $A_0$-$A_1$. Because of the three linear shapes of the linear segments LS1, LS2, and LS3, there is no curvilinear segment provided as a connector 20. Depending on the offset of the apices A1 and A2 to each other circumferentially and longitudinally, the length of linear segments LS2 and LS3 may be different from each other or zero for one or both. In FIG. 3C, however, a curvilinear connector 20C can be utilized. The width W1 of the connector 20C can be the same as the width W2 of the strut S2. Depending on the application of the helical stent 100, the width of the struts S1-S4 may be 50% larger or smaller than the width W1 of the connector 20. The width W3 of the intermediate member IS can be larger than the width W2 of the struts S1-S4 in order to control expansion of the helical stent 100.

Instead of the zig-zag strut pair Z1-Z2 shapes shown in FIG. 2, the helical stent 100 may have plurality of struts arranged as a plurality of undulations U (labeled as U1, U2, U3, U4, and $U_5$ in FIG. 4) disposed on the continuous helical path 10 of FIG. 1. The helical path 10 is formed by a plurality of arcuate sections AS (labeled as AS1-AS 5 in FIG. 4) about the axis $A_0$-$A_1$ where the plurality of undulations U includes a peak P and a trough T arranged between three individual struts ST1, ST2, and ST3, for example. In this alternate variation of the helical stent 100, there is at least one connector 20 connecting one of the undulations U to an adjacent undulation U.

The undulations U can be wave-like in pattern. The wave-like pattern can also be generally sinusoidal in that the pattern may have the general form of a sine wave, whether or not such wave can be defined by a mathematical function. Alternatively, any wave-like forms can be employed so long as it has amplitude and displacement. For example, a square wave, saw tooth wave, or any applicable wave-like pattern defined by the struts where the struts have substantially equal lengths or unequal lengths.

The connector 20 can connect any portion of the undulations U but it is preferred that the peaks P and troughs T of one arcuate section AS are connected to the peaks P and troughs T of an adjacent arcuate section AS, which are spaced apart along the axis $A_0$-$A_1$. In the most preferred embodiment, at least one connector 20 connects a peak P of one arcuate section AS to a peak P of an adjacent arcuate section AS where the peaks P are offset circumferentially with respect to the axis $A_0$-$A_1$. Where the peaks P are not offset, the connector 20 extends substantially parallel with respect to the axis $A_0$-$A_1$ of the helical stent 100. As noted above, however, it is most preferred that at least one connector 20 extends obliquely with respect to a direction extending parallel to the axis $A_0$-$A_1$. The connector 20, for example, can also be configured to connect one peak P of one arcuate section AS4 to a trough T of another arcuate section AS5 as indicated by connector 22 in FIG. 4, which is oblique to the direction of the axis $A_0$-$A_1$. The connector 20 can also be from the peak P of one section AS4 to the trough of another section AS5 via a connector 24 that is generally parallel to the direction of the axis $A_0$-$A_1$. Moreover, at least one connector 20 is configured to be absorbed upon exposure to biological tissue.

Figure 4:
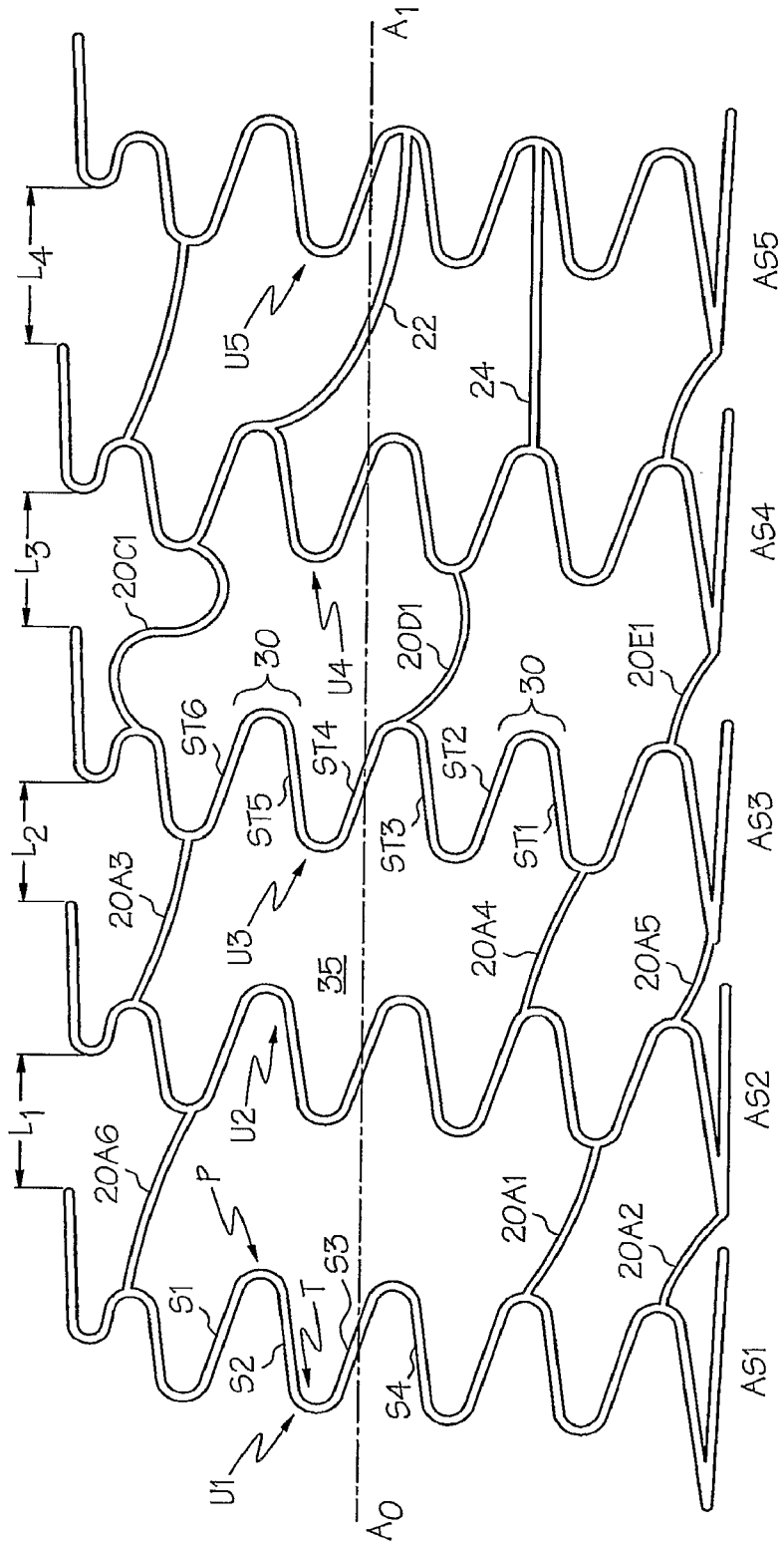
FIG. 4 illustrates the stent structure of a variation of the embodiment of FIG. 1.

There are variations for the connectors 20 in the helical stent 100 illustrated in FIG. 4 that are worthy of further discussion. One type of connector is generally similar to the connector 20A illustrated in FIG. 3A while variations of the connector 20A are delineated as 20A1, 20A2, 20A3, 20A4, 20A5, and 20A6 in FIG. 4. A wave like connector 20C1 can also be utilized along with a curvilinear connector 20D1. The connectors may be arranged in a repeating pattern or they may be arranged in a non-repeating pattern in the helical stent 100. In the preferred embodiment, the number of struts S1-S4 disposed above and below connectors 20 (between sequential connectors 20 connecting arcuate sections AS) can be the same. For example, as illustrated in FIG. 4 by arcuate section AS3 which includes repeating undulations D3 (each having two struts and a loop 30) that are helically wound along and about the axis $A_0$-$A_1$. There are preferably nine undulations U in each circumferential winding or arcuate section AS1-AS5 and the undulations U are interdigitated. With reference to arcuate sections AS2-AS4, a connector 20 is located every three undulations therebetween, and each connector 20 extending from arcuate section AS3 joins undulations U on the adjacent arcuate sections AS2 and AS4, which are one and one-half pitches away (or three struts over from directly across, as illustrated by the struts identified as ST1-ST3 of the arcuate section AS3 between the connector 20A4 and the connector 20D1). All connectors 20 in the central portion AS3 of the helical stent 100 preferably extend in the same direction, longitudinally crosswise across the helical space between adjacent arcuate sections AS. This preferred exemplar embodiment provides a very symmetrical distribution of connectors 20 in at least the longitudinal middle of the helical stent 100. In particular, referring to FIG. 4, in an area 35 which is a space bounded by portions of AS2 and AS3 and by connectors 20A3 and 20A4, tracing a path from any one connector disposed on the $A_0$-facing side of AS3 (e.g., connector 20A4) to the nearest connector on the $A_1$-facing side of AS3 (e.g., connector 20D1) and counting struts disposed between the connectors 20, there are counted three struts (identified as ST1-ST3 in FIG. 4). Likewise, traveling from any one connector (e.g., connector 20A3) to the next connector (e.g., connector 20D1) in an opposite direction around area 35 also traverses exactly three struts (identified as ST6, ST5, and ST4 in FIG. 4). It is believed that a design having equal number struts between connectors as defined herein provides advantageous characteristics with regard to flexibility and strength. In the preferred embodiment, the number of struts in the clockwise or counterclockwise direction around an area (an area 35 for example) can range from 3 to 7. Alternatively, the number of struts in one direction can be different from the number of struts in the other direction. For example, in section AS3, the number of struts between connector 20A3 and connector 20C1 (in a counter-clockwise direction) is one whereas the number of struts between connector 20A6 to connector 20A4 is five (in a clockwise direction).

In one preferred embodiment, about 20% to about 80% of the total number of connectors 20 for the helical stent 100 are bio-resorbable. In another preferred embodiment, all of the connectors 20 are bio-resorbable.

One suitable bio-resorbable material for the connector 20 can be one or more of a metal alloy shown and described in U.S. Pat. No. 6,287,332 or the metal alloy shown and described in U.S. Pat. No. 7,879,367, which are incorporated by reference in their entirety. Preferably, the metallic bioabsorbable material is selected from a first group consisting essentially of: magnesium, titanium, zirconium, niobium, tantalum, zinc, silicon, and combinations thereof. Also provided are mixtures and alloys of metallic bioabsorbable materials, including those selected from the first group. Various alloys of the materials in the first group can also be used as a metallic bioabsorbable material, such as a zinc-titanium alloy, for example, as described in U.S. Pat. No. 6,287,332 to Bolz et al. The physical properties of the alloy can be controlled by selecting the metallic bioabsorbable material, or forming alloys of two or more metallic bioabsorbable materials. For example, the percentage by weight of titanium can be in the range of about 0.1% to about 1%, which can reduce the brittle quality of crystalline zinc. Without being bound to theory, it is believed that the addition of titanium leads to the formation of a $Zn_{15}Ti$ phase. In another embodiment, gold can be added to the zinc-titanium alloy at a percentage by weight of about 0.1% to about 2%, which is believed to result in a further reduction of the grain size when the material cures and further improving the tensile strength of the material.

In some embodiments, the metallic bioabsorbable material can be an alloy of materials from the first group and a material selected from a second group consisting essentially of: lithium, sodium, potassium, calcium, iron, manganese, and combinations thereof. The metallic bioabsorbable material from the first group can form a protective oxide or passivation coating upon exposure to blood or interstitial fluid. The material from the second group is preferably soluble in blood or interstitial fluid to promote the dissolution of the oxide coating. Also provided are mixtures and alloys of metallic bioabsorbable materials, including those selected from the second group and combinations of materials from the first group and the second group.

Briefly, the combination of metal materials can be a metal alloy, the selection of the alloy constituents serving to attain the prerequisite of biocompatible decomposition. Consequently, the metal alloy may consist of a combination of material that will decompose in the body comparatively rapidly while forming harmless constituents. Such alloy may include a component A which covers itself with a protective oxide coating. This component A is selected from one or several metals of the group of magnesium, titanium, zirconium, niobium, tantalum, zinc, silicon, or combinations thereof. For uniform dissolution of the protective oxide coating to be attained, a component B is added to the alloy, possessing sufficient solubility in blood or interstitial fluid, such as lithium sodium, potassium, calcium, iron or manganese. The corrosion rate is adjusted by way of the composition so that gases, such as hydrogen, which evolves during the corrosion of lithium, sodium, potassium, magnesium, calcium or zinc dissolve physically and essentially not forming any macroscopic gas bubbles. Other alloys can be utilized such as, for example, an alloy of lithium and magnesium in the ratio of about 60:40; a sodium-magnesium alloy; zinc-titanium alloy—the percentage by weight of which is in the range of about 0.1% to about 1% with gold being optionally added at a percentage by weight of about 0.1% to about 2%. Further details relating to these metallic bioabsorbable materials are described in U.S. Pat. No. 6,287,332 to Bolz et al., which is incorporated herein by reference in its entirety.

Other materials for either the stent framework or the connectors can include biodegradable polymers such as polylactic acid (i.e., PLA), polyglycolic acid (i.e., PGA), polydioxanone (i.e., PDS), polyhydroxybutyrate (i.e., PHB), polyhydroxyvalerate (i.e., PHV), and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes. As used herein, the term "bio-resorbable" includes a suitable biocompatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bio-resorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above.

The stent 100 can be made by various techniques. One technique is described with reference to FIGS. 5A-5C. In FIG. 5A, a hollow generally tubular tube stock 40 of a suitable material (e.g., Nitinol or Elgiloy) is illustrated as having a portion 42' of the tube stock 40 removed to provide at least one opening 42 and preferably a plurality of openings. The opening 42 is partly covered by a bio-resorbable metallic plug 44 that can be coupled to the tube stock 40, as illustrated in FIG. 5B. In the preferred embodiment, the plug 44 is a resorbable metal plug smaller than the opening 42. At this point, the plug 44 is bonded to the tube stock 40 by a suitable brazing, heating, welding, or soldering process that joins the plug 44 to the edges of the opening 42. Where the tube stock 40 is Nitinol, the joining process can be utilized by the one shown and described in U.S. Pat. No. 5,242,759, which is incorporated by reference in its entirety herein. Thereafter, the tube stock 40 is cut to form a helical stent 100 in an unexpanded configuration where the helical stent 100 outside diameter is smaller than the expanded configuration.

The process to join the metallic plug 44 involves applying to the surface of the tube stock 40 a suitable flux having an activation temperature below a predetermined annealing temperature of the tube stock 40. The activated flux has a composition of ingredients suitable for removing contaminants from the surface of the tube stock 40 and for further removing at least portions of the titanium from the surface while leaving the nickel therein. The flux with the contaminants and at least portions of titanium suspended therein are removed from the tube stock 40 surface while leaving nickel to form a nickel-rich interface surface for bonding to another metal layer such as a solder material. As a result, a low temperature solder material can flow on the nickel-rich interface surface to form a good metallic bond without affecting the shape memory or superelastic properties of the tube stock 40. The removal of contaminants can include at least partially leaching titanium from the tube stock 40 alloy surface with the flux heated to its activation temperature then cooling the flux to form a solid coating of the flux on the nickel-rich interface surface after the flux-heating. To strengthen the metallic bond, the flux is scrubbed from the alloy member surface to remove the suspended contaminants and titanium from the nickel-rich interface surface. Additional flux is applied to the scrubbed nickel-rich interface surface to leach additional titanium and to remove any remaining contaminants or oxidation. A metal such as a tin-silver solder material is flowed to the nickel-rich interface surface of the tube stock 40 to displace from the interface surface the coating of flux with the contaminant and titanium suspended therein. Any remaining residual flux is then cleaned from the alloy member surface after the application of the solder material thereto. Basic surface preparation is made to both the tube stock 40 and the plug 44. Then a molten solder having a melting point below a predetermined annealing temperature of the tube stock 40 is applied to the nickel-rich interface surface. The plug 44 is positioned in contact with the molten solder, and cooling the molten solder to join the tube stock 40 to the plug 44. The flux utilized can be an aluminum flux paste having at least one of tin chloride, zinc chloride, hydrofluoric acid, ethanolamine, and combination thereof as active ingredients. The solders utilized in the soldering method can be selected from the group of gold, nickel, indium, tin, silver, cadmium, lead, zirconium, hafnium, and combinations thereof. The soft solder is preferably a material with a melting temperature below about 425 degrees Celsius such as, for example, silver solder.

After the tube stock 40 has been joined with plug 44 to form a one-piece unitary member 46 (with a portion of the member 44 illustrated in FIG. 5C), the unitary member 46 is cut by a suitable cutting technique, such as, for example, laser cutting, electro-discharge-machining, etching, as is known to those skilled in the art, one of which is shown and described in U.S. Pat. No. 6,572,647, which is incorporated by reference herein.

In the cutting process of FIG. 5C, the unitary member 46 is cut according to the design illustrate in FIG. 1, for example, with portions delineated by hatched lines indicating an example portion of the material removed in the cutting process. In particular, the cutting of the tube stock 40 is designed so that the portion forming the connector 20 between the undulations U1 and U2 coincides with the resorbable plug 44, shown with dashed lines in FIG. 5C.

Figure 5D:
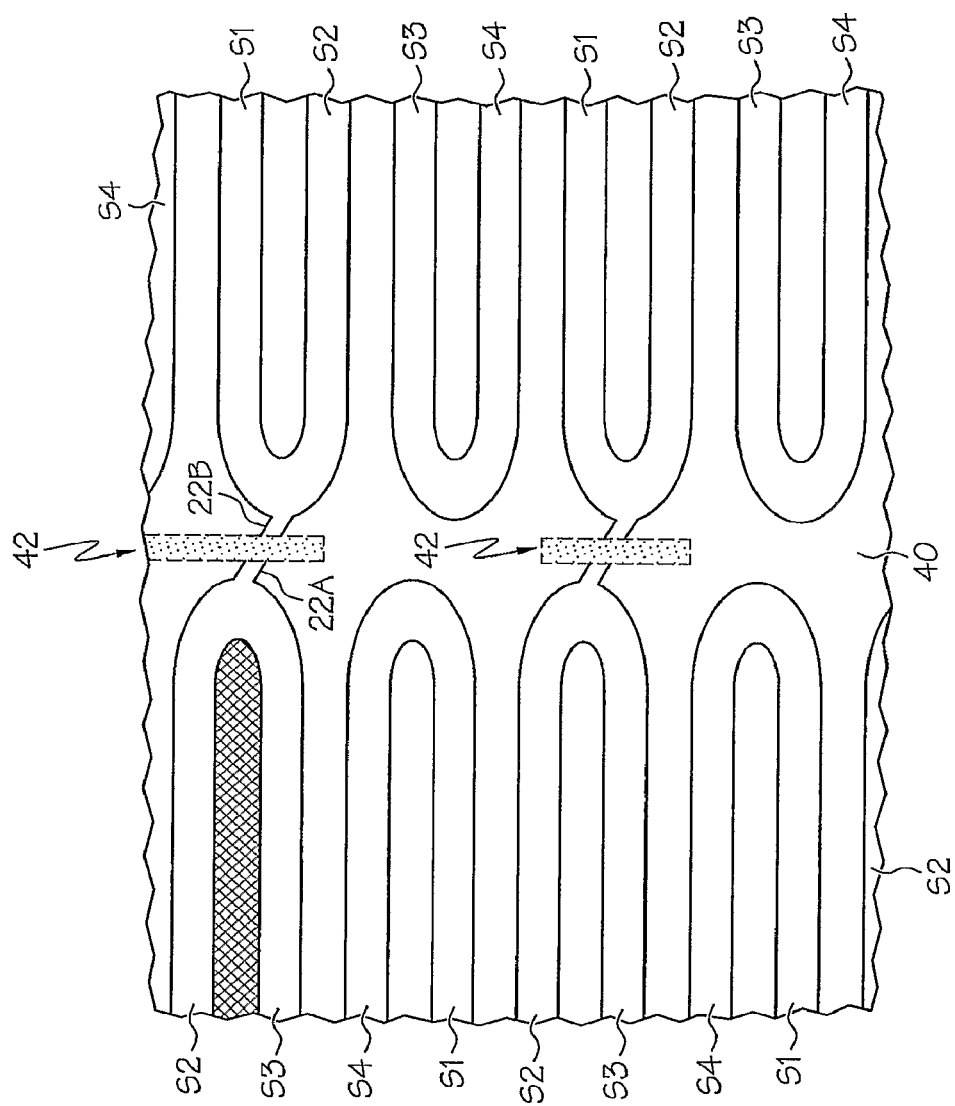

Another technique to form a resorbable connector other than a metal (which is dissimilar to the tube stock 40 and which may be resorbable or non-resorbable) can be as follows. A tube stock 40 (illustrated in FIG. 5A) has an opening 42 formed therein by a suitable machining process. Instead of joining a resorbable metal to the opening 42, as illustrated in FIG. 5B, the struts S1-S4 are cut into the tube stock 40 as illustrated in FIG. 5D with the opening 42 present in the surface of the tube stock 40. To facilitate a connection between the undulations, vestiges 22A and 22B of the connector 20 can be provided. After the cutting and suitable surface preparation, a suitable non-metallic material (including non-resorbable material but is preferably resorbable) such as those described above and others known to those skilled in the art can be used to connect the connector vestiges 22A and 22B together (with suitable geometry such as, for example, barbs, hooks, or flares to facilitate adherence to a non-metallic connector). The non-metallic resorbable material preferably is a polymer with sufficient strength to form a connection between the undulations that can endure delivery and implantation in a mammalian host for an acceptable period of time before resorption by the host. In one embodiment, bio-active agents can be added to the polymer or to the metal alloy for delivery to the host's vessel or duct. The bio-active agents may also be used to coat the entire stent. A coating may include one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); antiproliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors including CD inhibitors, thymidine kinase ("TK") and other agents useful for interfering with cell proliferation the family of bone morphogenic proteins ("BMPs"), BMP-2, BMP-3, BMP-4, BMP-5, BMP-6 (Vgr-1), BMP-7 BMP-8, BMP-9, BMP-IO, BMP-I, BMP-12, BMP-13, BMP-14, BMP-15, and BMP-16. Desirable BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA encoding them.

Cells can be of human origin (autologous or allogeneic) or from an animal source (xenogeneic), genetically engineered if desired to deliver proteins of interest at the deployment site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The preferred stents may also be used as the framework for a vascular graft. Suitable coverings include nylon, collagen, PTFE and expanded PTFE, polyethylene terephthalate and KEVLAR®, ultra-high molecular weight polyethylene, or any of the materials disclosed in U.S. Pat. Nos. 5,824,046 and 5,755,770, which are incorporated by reference herein. More generally, any known graft material may be used including synthetic polymers such as polyethylene, polypropylene, polyurethane, polyglycolic acid, polyesters, polyamides, their mixtures, blends and copolymers.

In the preferred embodiments, some or all of the connectors are bio-resorbed while leaving the undulating strut configuration essentially unchanged. In other embodiments, however, the entire helical stent can be resorbed in stages by a suitable coating over the resorbable material. For example, the connectors can resorb within a short time period after implantation, such as, for example, 30 days. The remaining helical stent framework (made of a resorbable material such as metal or polymers) can thereafter resorb in a subsequent time period, such as, for example, 90 days to 2 years from implantation. For example, in the design graphically illustrated in FIG. 6, a stent 200 has an end section ES with arcuate sections AS1-AS4 continuing on to another end of the stent 200 (not shown) (as with FIGS. 1 and 2, the continuous helical path of the arcuate sections AS is not shown for clarity). In some applications, the use of the end section ES may facilitate crimping of the stent 200 into a loading device. In such situation, the end section ES is connected to the helical arcuate sections AS1-AS4 via a non-resorbable material 30, preferably the same material as the undulations. The remainders of the arcuate sections that form the helical configuration are coupled to each other via a resorbable connector 20.

One technique of controlling the period of time after delivery that the arcuate sections or connector remain covered, and therefore not subject to resorption or degradation, can be provided by using a suitable material that changes chemical structure upon exposure to a particular activating wavelength of radiation (e.g., UV or visible light). In one embodiment, the bio-resorbable structure (the struts or connector) is provided with a water repellant coating that prevents body fluids from degrading the resorbable material. Once exposed to the activating wavelength of radiation, the water repellant coating dissolves or becomes porous so that hydrolytic or enzymatic degradation of the underlying resorbable material can begin. In another example, exposure to a specific wavelength of light causes the light-activated material to change structure to thereby allow separation between the cover material and the underlying resorbable material. In an example, the activating radiation can be UV light, visible light or near infrared laser light at a suitable wavelength (e.g., 800 nanometers) at which tissues are substantially transparent. In a particular embodiment, the coating material may be polyethylene with a melting point of about 60 degrees Celsius mixed with biocompatible dyes that absorb radiation in the 800 nm range. Such dye can be Indocyanine green, which is a dye that absorbs radiation around 800 nm and is biocompatible, and will absorb the light energy and thereby raise the temperature in the polymer to about 60 degrees Celsius or higher. Upon attainment of the melting point temperature, the polymer structurally weakens thereby allowing the coating to lose integrity (i.e., crack, peal or otherwise become porous or at least a portion of the surface) thereby allowing biological fluid to come into contact with the underlying resorbable material and initiate the resorption process. It is noted that the embodiment where the underlying stent framework and connectors are of a resorbable material, the stent framework and connectors would eventually resorb within a specified time period due to natural degradation of the coating. The technique described herein, however, allows for acceleration of the resorption or degradation process.

Figure 6:
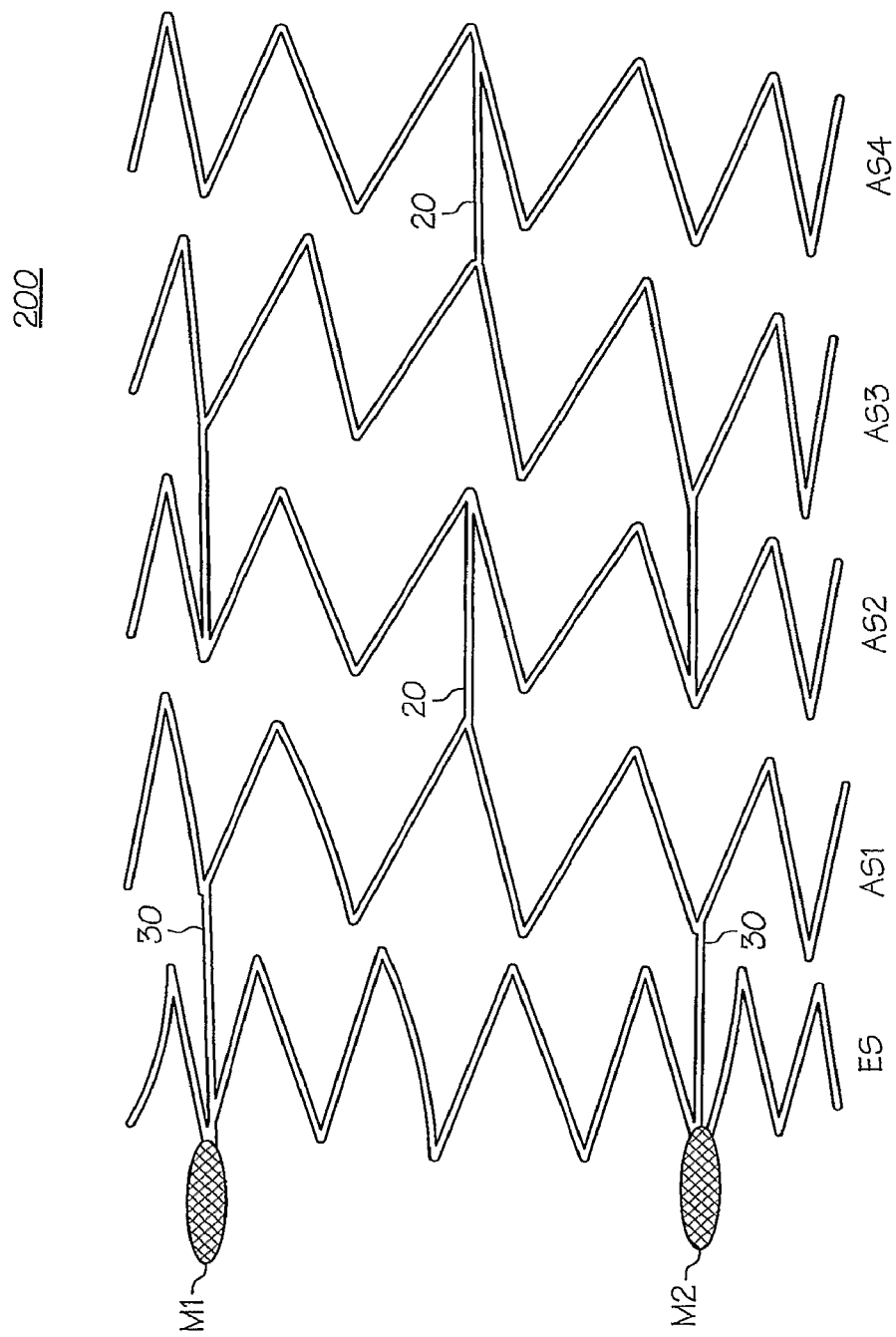
FIG. 6 illustrates a variation of the stent structure of the embodiment of FIG. 1.

As also illustrated in FIG. 6, markers M1 and M2 can be provided for all of the embodiments described herein. The marker M1 can be formed from the same material as the stent 200 as long as the material is radiographic or radiopaque. The marker material can also be formed from gold, tantalum, platinum for example. The marker M1 can be formed from a marker material different from the marker M2.

The devices described herein can be, with appropriate modifications, delivered to an implantation site in a host with the delivery devices described and shown in U.S. Pat. Nos. 7,993,384, 7,758,624, 6,939,352, or 6,866,669, which are incorporated by reference herein in their entirety.

The design of the preferred embodiments is believed to be advantageous over the known partially bio-resorbable stent rings in that, where all of the connectors are designed to be resorbed, there is only one remaining structure in the vessel or duct of the host. In contrast, with the known partially resorbable stent rings, once all of the connectors are resorbed in tissue, there is a multiplicity of separate rings unconnected to each other, each of which can migrate.

Figure 7:
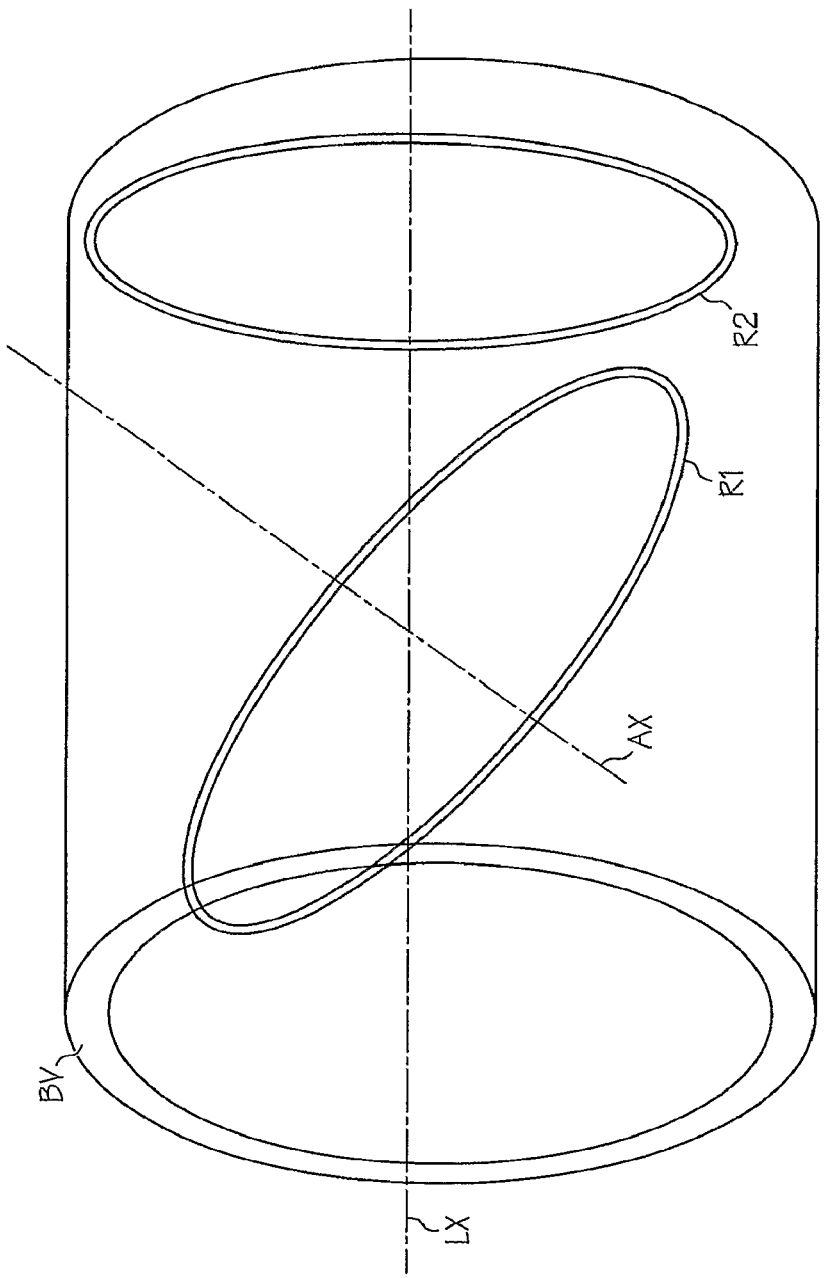
FIG. 7 illustrates a potential problem with a known stent.

It is believed that another possible problem that may arise with the partially biodegradable ring stent is that, once the connectors have resorbed in the body, the stent becomes a collection of discrete annular rings in the vessel or duct. As illustrated in FIG. 7, such separate rings R1 and R2, when distorted or compressed by an external force (such as pressing on the carotid artery where such stent is implanted or simply due to compression of the vessel or duct from body, joint movements or muscle movements). As such each ring may be twisted into a configuration where the rings are no longer co-axial with the duct or vessel BV. This problem is illustrated in FIG. 7 where the axis AX of one of the rings R1 is oblique to the longitudinal axis LX of the vessel or duct BV. Once the ring R1 is in this position, it is believed that the ring can no longer recover to its original coaxial position as ring R2. Thus, it is believed that this situation could potentially lead to a partial occlusion of the vessel.

Thus, the helical stent 100 and the various embodiments (with some embodiments more preferable than others) provide the ability to resist migration in the host vessel or duct in the event that the connectors between helical segments are absorbed before tissue ingrowth of the host vessel is able to securely retain the stent to the host's vessel. Additionally, the preferred embodiments alleviate the possible problem of ring stent occluding a vessel when the ring is moved or contorted (e.g., by an external force such as compression or by the movement of the host's joints or muscles). Further, the use of at least one helix with a small amount of connectors (e.g., in the situation where not all of the connectors are bio-resorbable) or no connectors allows for enhanced flexibility while implanted in the host.

Moreover, it is believed that the various embodiments allow for an unexpected advantage in that the flexibility of the preferred stents can be configured to change subsequent to implantation in a biological duct or vessel either preconfigured in the stent or changed subsequently by a clinician. That is, the resorbable connectors permit the stent to have a first spring constant in an unimplanted condition and a second different spring constant in an implanted condition after a predetermined period of time or after the resorption of the stent or connector is accelerated by an energy device external to the host. In the preferred embodiments, the first spring constant is preferably a higher spring constant so as to maintain a desired axial spacing L1, L2, L3, and L4 generally constant (as illustrated in FIG. 4), which is believed to prevent intrusion or substantial prolapse of the biological tissue in between the axial spacing. The spring constant or spring rate can be changed subsequently as part of the stent's initial configuration or via an agent (e.g., UV light or laser light) external of the host.

Although the various embodiments have been described in relation to a framework that define essentially a portion of a tube using wire like members, other variations are within the scope of the invention. For example, other embodiments of the framework may define different cylindrical sections with different outer diameter; the framework may define a cylindrical section coupled to a conic section; the framework may define a single cone; the wire-like members may be in cross-sections other than circular such as, for example, rectangular, square, or polygonal.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A medical device comprising:
   a covered stent comprising a plurality of arcuate sections formed from a stock material; and
   a connector coupling adjacent arcuate sections, the connector comprising a first bioresorbable material different from the stock material.

2. The medical device of claim 1, wherein the first bioresorbable material comprises an alloy.

3. The medical device of claim 2, wherein the alloy comprises a material that promotes passivation or corrosion.

4. The medical device of claim 3, wherein the alloy generates hydrogen gas during resorption.

5. The medical device of claim 4, wherein the hydrogen gas does not form macroscopic bubbles.

6. The medical device of claim 5, further comprising a second bioresorbable material.

7. The medical device of claim 6, wherein the second bioresorbable material comprises a nonmetallic material.

8. The medical device of claim 7, wherein the second bioresorbable material further comprises a bioactive material, and wherein the second bioresorbable material exhibits a faster degradation rate than the first bioresorbable material.

9. The medical device of claim 8, further comprising a light-sensitive, degradation-retarding coating.

10. The medical device of claim 2, further comprising a second bioresorbable material.

11. The medical device of claim 10, wherein the second bioresorbable material further comprises a bioactive material, and wherein the second bioresorbable material exhibits a faster degradation rate than the first bioresorbable material.

12. The medical device of claim 11, further comprising a light-sensitive, degradation-retarding coating.

13. The medical device of claim 2, further comprising a light-sensitive, degradation-retarding coating.

14. The medical device of claim 2, further comprising a second bioresorbable material that comprises a nonmetallic material.

15. The medical device of claim 14, wherein the second bioresorbable material further comprises a bioactive material, and wherein the second bioresorbable material exhibits a faster degradation rate than the first bioresorbable material.

16. The medical device of claim 15, further comprising a light-sensitive, degradation-retarding coating.

17. The medical device of claim 2, further comprising a second bioresorbable material.

18. The medical device of claim 1, wherein after implantation the covered stent exhibits a first spring constant that changes to a second spring constant as the first bioresorbable material resorbs.

19. The medical device of claim 18, wherein the first bioresorbable material comprises an alloy.

20. A medical device comprising:
   a covered stent including a plurality of arcuate sections;
   a connector between adjacent arcuate sections, the connector comprising:
      a first bioresorbable material comprising an alloy, the alloy comprising a material that promotes passivation or corrosion, wherein the alloy generates hydrogen gas during resorption, and wherein the hydrogen gas does not form macroscopic bubbles;
      a second bioresorbable material comprising:
         a bioactive material; and
         a nonmetallic material, wherein the second bioresorbable material exhibits a faster degradation rate than the first bioresorbable material; and
      a light-sensitive, degradation-retarding coating,
   wherein after implantation the covered stent exhibits a first spring constant that changes to a second spring constant as one of the first bioresorbable or the second bioresorbable material resorbs.

* * * * *